(12) United States Patent
Lee

(10) Patent No.: US 6,596,502 B2
(45) Date of Patent: Jul. 22, 2003

(54) KIT AND METHOD FOR DETECTING FECAL PARASITES

(75) Inventor: Martin Jerome Lee, Jerusalem (IL)

(73) Assignee: Lee Research Laboratory, Inc., Asheville, NC (US)

( * ) Notice: Subject to any disclaimer, the term of this patent is extended or adjusted under 35 U.S.C. 154(b) by 104 days.

(21) Appl. No.: 09/808,017

(22) Filed: Mar. 15, 2001

(65) Prior Publication Data

US 2002/0132270 A1 Sep. 19, 2002

(51) Int. Cl.[7] .............................................. G01N 33/569
(52) U.S. Cl. .................... 435/7.22; 435/7.1; 435/7.94; 435/288.1; 435/962; 435/970; 435/975; 436/514; 436/518; 436/528; 436/808; 436/810; 436/825; 422/56; 422/58; 422/61; 422/102
(58) Field of Search .................................. 436/514, 518, 436/528, 808, 810, 825; 435/7.22, 7.1, 7.94, 288.1, 962, 970, 975; 422/56, 58, 61, 102

(56) References Cited

U.S. PATENT DOCUMENTS 4,200,690 A * 4/1980 Root et al.
4,842,826 A * 6/1989 Guala
5,503,983 A  4/1996 Rosoff et al.
5,602,040 A * 2/1997 May et al.

FOREIGN PATENT DOCUMENTS

WO  WO 99/22239 A1  5/1999
WO  WO 00/17647 A1  3/2000

OTHER PUBLICATIONS

William E. Aldeen et al, "Comparison of Nine Commercially Available Enzyme–Linked Immunosorent Assays for Detection of *Giardia lamblia* in Fecal Specimens". Journal of Clinical Microbiology, vol. 36, No. 5, pp. 1338–1340, May 1998.

Lynne S. Garcia et al, "Detection of *Giardia lamblia*, Entoamoeba histolytica/Entamboeba dispar, and *Cryptosporidium parvum* , Antigens in Human Fecal Specimens Using the Triage Parasite Panel Enzyme Immunoassay" Journal of Clinical Microbiology, vol. 38, No. 9 pp. 3337–3340, Sep. 2000.

Susan Sharp et al, "Evaluation of the Triage Micro Parasite Panel for Detection of *Giardia lamblia*, Entamoeba histolytica/Entamoea dispar, and *Cryposporidium parvum* in Patietn Stool Specimens" Journal of Clinical Microbiology, vol. 39, No. 1, pp. 332–334, Jan. 2001.

* cited by examiner

Primary Examiner—Bao-Thuy L. Nguyen
(74) Attorney, Agent, or Firm—Browdy and Neimark, P.L.L.C.

(57) ABSTRACT

The invention concerns a home kit and a method for detection of the presence of a fecal parasite in a stool.

20 Claims, 2 Drawing Sheets

KIT AND METHOD FOR DETECTING FECAL PARASITES

FIELD OF THE INVENTION

The present invention is generally in the field of kits, and more specifically concerns kits for domestic use for the self-detection of various physiological conditions.

BACKGROUND OF THE INVENTION

Parasitology is one of the very few remaining tests in clinical medicine which relies on the visual recognition skills of a trained technologist. It involves, in fact, two visual recognition skills. One is the identification of particular morphological features characterizing an organism as belonging to a certain species, and being able to recognize it by name. The other, and much more difficult skill is the ability to recognize old, young, damaged, deformed, or even partially degraded organisms—perhaps occurring only at the edge of a microscopic field—and know that it is a particular parasite. Such being the case, a negative result for a parasitology test only indicates that no parasite was found, and can not be conclusive that a patient is negative for parasites.

The problem of parasite identification for the laboratory is additionally difficult due to the fact that parasite frequency can vary widely, and may not have any relation to severity of disease. Parasite reports are typically graded from rare to many. It is possible, in fact for a person to have a serious parsitological infestation, but to have only infrequent, periodic, or occasional shedding of parasitic organisms. In the case of low frequency of occurrence in the stool, organisms may or may not be present in the particular specimens being examined under the microscope.

The problem of parasite identification for the laboratory is additionally complicated due to the fact that transportation of specimens from the patient to the clinical laboratory is usually delayed and during this delay the parasites may die or be degraded, thus decreasing even further the chances of identification.

Thus, the situation exists where many clinical laboratories fail to detect parasites which, in fact, are present in patient specimens. Clinical laboratory surveys in the United States frequently report a positive prevalence of parasites of 1–3%, and rarely over 5%. Yet various published studies by specialty, or university based laboratories, show that the true positive rate can be as much as 4- or 5-fold higher than In response to this situation, parasitologists have developed methods of concentrating parasites and staining them with contrasting colors so as to improve recognition ability. Thus, a concentration procedure followed by a trichrome staining procedure has been developed as the standard method of properly performed parasitology analysis. This method, however, is laborious and time consuming. It is, therefore, not done by all labs all the time, in spite of recommendations to that effect. Even when performed, it does not address or solve all the problems mentioned above.

In recognition of this situation diagnostic device companies have developed tests for particular parasites. Notably tests for *giardia lamblia, entamoeba histolytica,* and cryptosporidium sp. are commercially available. These take two forms, either being an ELISA test (i.e.: Alexon-Trend, Inc), or fluorescent tagging of the organisms followed by direct microscopic examination (ie:Meridian Diagnostics, Inc). The problem with these tests, however, is that they attempt to identify a particular organism, and not all organisms or the overall presence of parasites. Furthermore these tests require laboratory procedures and the intervention of skilled technicians.

The nature of parasite examination, and prevalence in the world, divides the parasites into two large groups: protozoans, and worms and eggs. Protozoans are single celled organisms, and are the most common parasites found in developed countries of the world. They are, also, as a rule, smaller than worms and eggs, and are examined on high power (40×) of the microscope. Worms and eggs on the other hand are multi-cellular organisms, and are very common in underdeveloped countries of the world. They are, as a rule, larger than protozoans and are examined at low power (10×) of the microscope.

What is needed by medical science and the market, therefore, are two tests—one for protozoans, and one for worms and eggs. It would be sufficient to identify those specimens which are positive and differentiate them from those that are negative. It would be even more advantageous, however, to identify specifically those particular parasites which are present in each specimen.

SUMMARY OF THE INVENTION

The present invention is based on the realization that there is a need for a non-invasive, fast, accurate, and user friendly method for diagnosing the presence of parasites, both protozoan and non-protozoan, in stool. The need is especially evident in view of the high false negative diagnosis of many standard laboratory tests and the high level of skill required to identify, under a microscope the instance and type of the parasite. The present invention is further based on the realization that detection of the presence of parasites in stool is of the type of detections which may be carried out at home, or at a doctor's clinic, without involving an analyzing laboratory, since the patient (or doctor) can easily understand a positive result of such a test, and proceeds to treat the parasite, with consultation with a doctor by the administration of anti-parasitic compounds. Furthermore, there is a great advantage of detecting parasites in fresh stool instead of waiting until the parasite reaches the laboratory resulting many times in non-viable or degraded parasites.

The present invention is further based on the realization that it is possible to develop a kit for such a non-invasive, reliable and home (and practitioner's office) testing.

Thus the present invention by its first aspect concerns a home kit for detection of the presence of a parasite in a stool sample, the kit comprising:

(a) a vessel for mixing a stool specimen with a diluting liquid to produce a diluted stool specimen;

(b) a housing holding within a substrate, the substrate comprising at least one zone containing at least one anti-parasitic antibody, the housing further comprising reagents for producing a visually detected reaction when an antibody-parasite antigen complex is formed, the housing further comprising at least one conveying means for receiving diluted stool specimen and transferring it to the anti-parasitic antibody containing zone of the substrate;

(c) the housing further comprises an indicator for showing the presence of the visually detected reaction.

Preferably the anti-parasitic antibodies are polyclonal, in order to ensure that they interact effectively with all varieties of a specific specie of parasites. The antibodies may be prepared by any method known in the art, for example, by immunizing an animal with a suitable parasite or an immunogenic portion thereof, and then collecting the antibodies produced. Where the antibody is monoclonal, it should be against a conserved epitope of the specific parasite spears which is common to any many varieties of the parasite species as possible.

The antibodies may be against an immunogenic epitope present on the external surface of the protozoa or non-protozoa parasite, or against an immunogenic epitope of a compound shed of secreted from the parasites, such as parasite eggs.

The term "home kit" in the context of the present invention refers to the fact that the kit of the invention, and the detection reaction produced therein, does not necessitate any complicated machinery for collecting the specimen and preparing it, for positioning the specimen in the kit, and for reading and interpreting the results—and typically, the results can be viewed by the naked eye, or by simple optical reactor. The term does not necessarily mean that the kit is only operable at home, since due to its non-invasiveness and it is easy, user friendly manner of operation, it can be also used in a practitioner's office or even in hospitals without involving an analytical laboratory.

The kit of the present invention comprises a vessel in which a small amount of stool specimen can be placed and diluted by a suitable diluting liquid. The vessel can then be sealed and the stool and diluting liquid shaken to produce a diluted stool specimen. The diluting liquid may be plain tap water, but according to a preferred embodiment of the invention the diluting liquid is, saline, distilled water, 10% formalin solution, sodium acetate solution with or without detergent and the like, and this diluting liquid is also provided as part of the kit's present invention, either a priori present inside the vessel or in a separate container.

The vessel may be for example in the form of a regular capped tube, having graduations, which indicate the volume of the raw stool specimen which is to be placed inside the tube, as well as the amount of the diluting liquid to be added.

The kit may also comprise a construction for collecting the stool, such as a disposable sheet to be placed inside a toilet bowl, a disposable vessel for stool collection, etc., as well as a scooping device, for example in the shape of a small spoon to pick a determined amount of stool. The scooping device (scoop) may be an integral part of the vessel's cap.

The kit's main component is a housing which holds within a substrate. For example the housing may be a plastic container. The substrate may be sandwiched between two layers of the plastic container. On a predefined zone of the substrate are present antibodies against at least one parasite, and by a preferred embodiment they are immobilized on that zone. Examples of the substrates are absorbent material such as nitrocellulose sheets, gel-films, cellulose acetate, fiberglass sheet, paper, agarose gels, and in general any media featuring capillary force or absorbent forces of fluid. Typically the housing has at least one conveying means which can receive the diluted stool specimen and transfer it to said zone. The conveying of the liquid may be by capillary or absorbing flow, which are due to the inherent properties of substrate, or the inherent properties of a specifically desired layer or by the construction of specific flow channels which bring the fluid to the antibody-containing zone.

By one option the conveying means are a combination of an opening in the container which opening is associated with a construction which can transfer to diluted stool specimen to the zone on the substrate which holds the anti-parasite antibody and where the antibody-antigen interaction takes place. For example, the conveying means are in the shape of an opening in the housing through which a small amount of the diluted stool can be poured. The stool is then transferred to the antibody containing zone of the substrate, for example, by capillary forces either of the substrate itself (which is made of absorbent material) or by capillary or absorbent forces of a specially designed layer which sole purpose is to transfer the diluted stool to the antibody-containing zone, or by flow in specially designed channels.

By another option the conveying means is an absorbent material or material composed of capillaries which protrudes out of the housing, for example, an absorbent wick protruding out of an opening in the housing. In such a case the protruding substrate material is dipped in the diluted stool and due to capillary forces the liquid is transferred to the antibody-containing zone which is present inside the housing.

The anti-parasite antibodies may be immobilized on the substrate by any interaction such as covalent bonds, hydrogen bonds, electrostatic forces contained within voids of beads, etc.

Typically, large particles have to be filtered out of the diluted stool before the diluted stool is conveyed to the antibody-containing zone of the substrate. Said filtering may take place in the vessel itself, for example by constructing a two part cap: the more distal part serving as a seal, which hermetically closes the vessel and allows the user to vigorously mix its contents. However, this cap may be opened fully or partially to expose below a filter sieve which can ensure that only relatively small particles are poured from the vessel into the convening means.

Alternatively, the housing itself may comprise said filtering sieve, which for example may be present either at the mouth of the opening of the convening means, or may be present as a continuous filter sieve layer above the substrate zone on which the anti-parasite antibodies are present.

By a preferred option where the substrate is an absorbent material, the stool particles may be sieved on its upper layers of the substrate so that a filtered specimen reaches the layer of immobilized antigen.

By one embodiment, the kit may comprise a single parasite in stool antigen and in such a case it can give a binary (yes/no) indication, whether the stool contains that parasite. Alternatively, the indication may be quantitative, for example, by giving three shades of the same color—a darker shade indicating "high" (amount of parasites in stool), than medium shade "medium", and light shade "low".

By a preferred embodiment, the kit of the present invention is used to detect a plurality of different parasites, and in such a case it is possible to determine, in a single assay, whether the individual has a parasite in his/her stool and which type.

Kits in accordance with a preferred embodiment are generally divided into two groups according to the parasites to be detected; kits or the detection of protozoa parasites and kits for the detection of non-protozoa parasites.

The kits for the detection of fecal protozoan parasites are for the detection of protozoa (single cell parasite): *Amoeba histolytica, Amoeba hartmanni, Amoeba coli, Amoeba nana, Giardia lamblia,* , Cryptosporidium sp., *Blastocystis hominis, Chilomastix mesnili, lodamoeba butschlii, Dientamoeba fragillis.*

The kits for the detection of fecal non-protozoan parasites are for the detection of Platyhelminthes (flat worms): flukes (liver, intestines, lungs and blood) and tapeworms (intestines), Nemathelminthes (round worms); Strongyloides, Trichuris, Trichinella, Pin worms, Ascaris, et al.

Preferably the kits of the invention are for the detection of protozoa parasites.

The kits of the invention may be used for human and veterinary usage. Many times domestic animals and pets suffer from the same parasite problems as humans and the kit of the invention may be used to detect parasites in animal stools.

Typically, regions of the substrate surrounding the zone on which the anti-parasite is immobilized are saturated by non-specific hydrophilic polymers such as bovine serum albumin, other proteins, or polyethylene glycol to block unspecific binding of the antibody to the substrate.

Interaction between the anti-parasite antibodies, a priori present in the kit, and parasites or parasitic components (for example, epitopes shed or secreted by parasites, for example, eggs which are present in the stool specimen, yields an antigen-antibody complex. In the kit of the invention the presence of such a complex should produce a visually detected reaction—i.e. a reaction which produces a visible indication, which may be viewed either by the naked eye, or by an optical reader. Examples of such a reaction is a color reaction (achieved by ELISA method) or a precipitation reaction which can easily be detected. A plurality of methods for producing visually detected reaction for antigen-antibody complexes are well known in the art, for example, as specified in "Immunoassay Handbook". by David Wild, $2^{nd}$ Edition, *Nature Publishing Group*, pp 159–175, 271–277). An example is indirect ELISA, a procedure which is used to identify the presence of the stool antigen utilizing, for example, antibodies against the parasites conjugated to a visually detectable moiety (such as gold particles) or conjugated to an enzyme producing a color reactor). Another possibility is by detection of the presence of antibody-antigen aggregates, by visually detectable precipitation reaction.

The indicator is typically an opening in the housing ("a window"), which allows direct viewing of the visually detected reaction. Typically the opening is immediately above the region on which the antibodies are immobilized. The view may be by the naked eye, for example, by the detection of a colored bar, or a colored dot, or alternatively may be viewed by an optical reader, to increase sensitivity.

Where a single parasite is to be detected, a single indicator can be used which when showing the indicator (color bar, dot, etc.) indicates that there exists the specific parasite in the stool.

Where a plurality of parasites are to be detected, a plurality of indicators (windows) can be used so that each indicator is associated with a single parasite. Alternatively, a single indicator giving different readings can be used wherein each reading is in accordance with the specific antigen-antibody complex formed and thus each reading is indicative of a different parasites, present in the sample.

For example, where five different parasites are to be tested, it is possible to construct a housing with five different and separate anti-parasite-antibody containing substrate zones, so that in each zone a different anti-parasite-antibody will be immobilized, and for each zone there will be associated a separate indicator. This will ensure that the visually detected reaction in each zone is specific to the anti-parasite antibody (and hence parasite) present on the substrate of said zone, and the indicator ("window") will simply be specifically associated with each zone. In the above case the housing may have a single means convening for example in the form of an absorbent layer.

The liquid stool specimen is poured into an opening, and due to the fact that the substrate is absorbent, capillary forces present in the absorbent material, cause transfer of the diluted stool specimen through all the separate zones on which are immobilized different anti-parasite antibodies. Then, the specific visually detected reaction is formed in each separate zone which reaction can be viewed by the specific indicator associated with that zone (for example by a "window" in the container through which a colored bead can be viewed).

In accordance with a preferred embodiment of the invention, the kit also contains internal control. The internal control is composed of those parasitic epitopes which specifically interact with the immobilized antibodies, present a priori, in the zone of the antibodies. The purpose of these, a priori, present parasitic antigens, is to form aggregates with the anti-parasitic antibody, to produce a visually detected reaction, in order to determine that the reagents used for producing the reaction are functioning properly.

The antibodies detected by the kit of the invention may be any antibody, monoclonal or polyclonal against a parasite.

As indicated above, polyclonal antibodies are preferred for ensuring that they react with all varieties of the species of parasites tested. Monoclonal antibodies are used and they should be directed against an epitope conserved in all varieties of the parasite species.

The present invention also concerns a method for detecting the presence of a parasite in a stool sample, the method comprising:

(a) obtaining a stool specimen;

(b) diluting the stool specimen with a diluting liquid to produce a diluted stool specimen;

(c) introducing the stool specimen into the kit of the invention; and (d) viewing the indicator, the presence of a visually detected reaction in the indicator, indicating the presence of the parasite in the stool.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
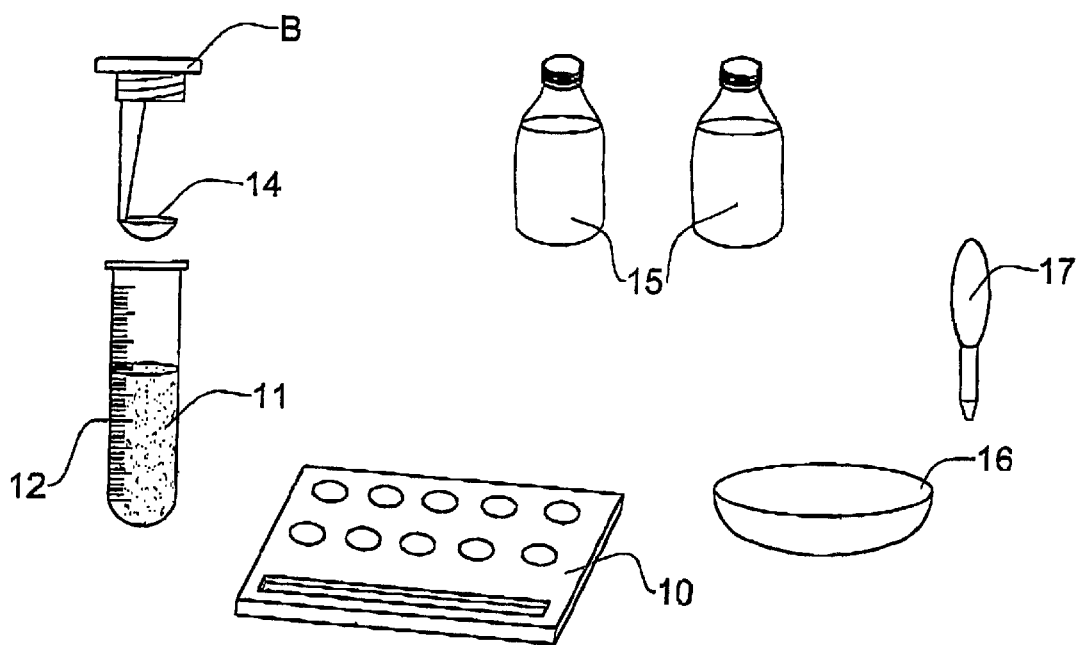
FIG. 1 shows a schematic representation of the components of the kit of the invention.

Reference is made to FIG. 1 which shows basically an example of the various components of the kit of the invention.

The main component of the kit of the invention is a housing 10 holding within a substrate on which are immobilized various anti-parasite antibodies, as will be explained in more detail in FIGS. 2 and 3 and on which, the detection actually takes place. In addition, the kit comprises a vessel 11 into which a stool specimen is placed. Typically it is capable of holding about 5–10 cc of liquid. Cap 13 of the vessel is engagable with vessel 11, and once closed can form a hermetically closed seal so that the vessel can be vigorously shaken to dilute the stool specimen with the diluting liquid. The vessels may be marked by graduations 12 which show the amount of liquid present within.

By the embodiment shown in FIG. 1, the cap 13 has as an integral part also scooping spoon 14 which can pick up a small amount of stool, and once the cap is fully engaged with the tube 11, the spoon is immersed inside the liquid in the tube and thus cause dilution of the stool. The kit also comprises liquid bottles 15 which may contain, for example, the diluting liquid, and in some cases, reagents required to produce a color reaction (to be specified in more detail hereinafter). Finally, the kit also contains a device 16, in the form of a small disposable container, for collecting the stool.

Where it is desired to add reagents present in bottle 15, the kit may also contain a small pipette 17.

Figure 2A:
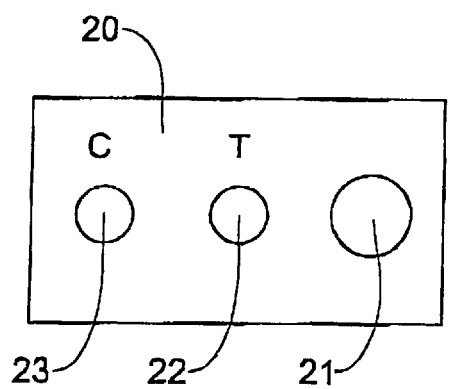
FIG. 2A shows one embodiment of the housing of the invention having the substrate fully contained within the housing, for detecting the presence of a single parasite in the stool.

Reference is now made to FIG. 2A which shows the housing of the kit of the present invention 20. Typically, the housing is made out of plastic material, and holds within an absorbent material such as nitrocellulose. In the housing, three openings are evident, 21, 22 and 23. Into opening 21, a minute amount of diluted stool sample is poured. Then, due to the capillary forces of the nitrocellulose substrate present within housing 20, the liquid advances towards opening 22 and 23. Opening 22 (T) is the test indicator and present above the region of the substrate on which the anti-parasitic antibodies against one species of parasites to be determined in the stool are immobilized. If the stool sample contains parasites or parasite portions reactive with the immobilized antibody on the substrate in region 22, an antibody-antigen aggregate is formed, which can be viewed, for example, as a dark dot in opening 22.

Opening 23 is a control zone C in opening 22, and in that zone, a priori, are present already aggregates of the parasitic antigens bound to the anti-parasitic antibodies. The purpose of opening 23 is to test the quality of the reagents in forming the visually detected reaction.

Once the aggregate of antibody-antigens are formed in test region T (and a priori present in control region C), they can be detected by any manner known in the art. In a manner, they are detected by the use of antibodies against parasite antigens (for example, antibodies of the same type as those immobilized to the substrate) which are conjugated to a detectable moiety. The detectable moiety for example may be a gold particle which may be visualized directly, or alternatively, may be an enzyme such as alkaline phosphatase, which can produce a color reaction if provided with its appropriate substrate such as para-nitro phenyl phosphate. Alternatively, other enzymes or other labels may be used.

The antibody coagulated to the detectable moiety may be added, after a phase of time (allowing the parasite antibody in the tested region to react with the parasitic antigen in the stool sample) to occur, simply by adding, from an external tube, the appropriate antibody to a detectable moiety.

By another option, the antibody conjugated to the detectable moiety (either with the gold particle or with the enzyme) may be present at a different layer than the layer on which the anti-parasite antibody is present, for example, present in a layer below that of the anti-parasite antibody. Between two layers there is present a dissolvable layer, which is slowly degraded by fluids in the specimen. This ensures that there is time for degradation of the layer, allowing first the parasite antigen in the stool sample to react with the immobilized antibody and only later the antibody conjugated to the detectable moiety is added.

Figure 2B:
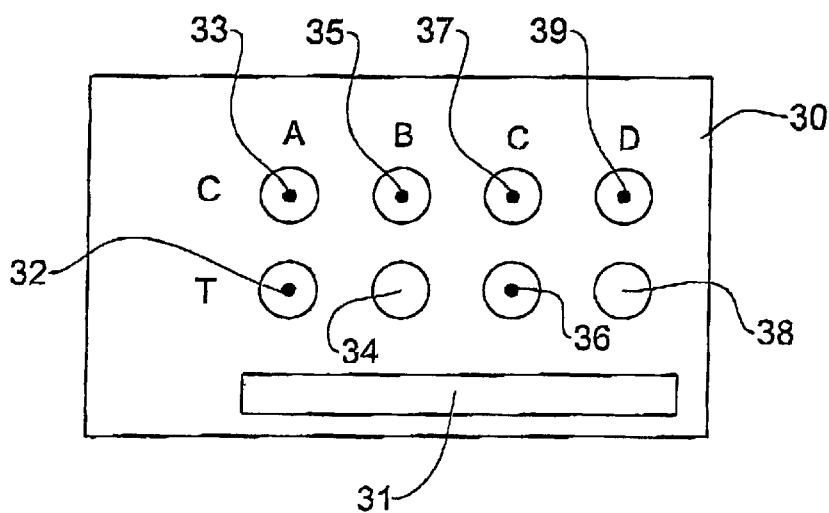
FIG. 2B shows another embodiment of the housing of the type shown in FIG. 2A for detecting the presence of a plurality of parasites in the stool.

FIG. 2B shows essentially the same construct as FIG. 2A, but for the detection of a plurality of parasites in stool, in the present case for the detection of four different protozoa allergies marked schematically as A, B, C and D. The housing 30 has an elongated opening 31 on which the sample is poured. Then, by capillary forces the fluid advances towards the other end of the housing. Openings 32, 34, 36 and 38 show test results, i.e. are above the zone of the substrate containing immobilized anti-parasite antibodies. Openings 33, 35, 37 and 39 are control openings, i.e. in above the zones of the substrates on which are immobilized, a priori, antigen-antibody aggregates. The reaction takes place essentially as explained in 2A above. In the present case, all the control openings have a dot indicator, indicating that the reagents properly work as they detected the a priori present antigen-antibody aggregates. In the test samples, there is an indicator in openings 32 and 36, indicating that the tested has both parasitic protozoa A and C.

Figure 3A:
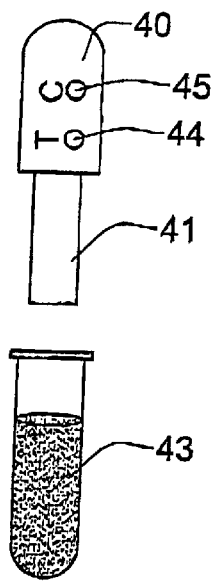
FIG. 3A shows an embodiment of a housing containing a substrate protruding out of the housing for detecting the presence of a single parasite in the stool.

Reference is made to FIG. 3A which shows another embodiment for the housing of the invention. Housing 40 contains within substrate, such as a nitrocellulose sheet, which protrudes, in the form of a wick 41 out of the end of the housing. Then, the protruding end of the substrate may be dipped inside the vessel 43 containing the diluted stool sample. As explained above, by capillary forces, the sample advances, and through openings 44 and 45, it can be determined whether a color reaction takes place both in the test (T) and the control (C) indicators (opening).

Figure 3B:
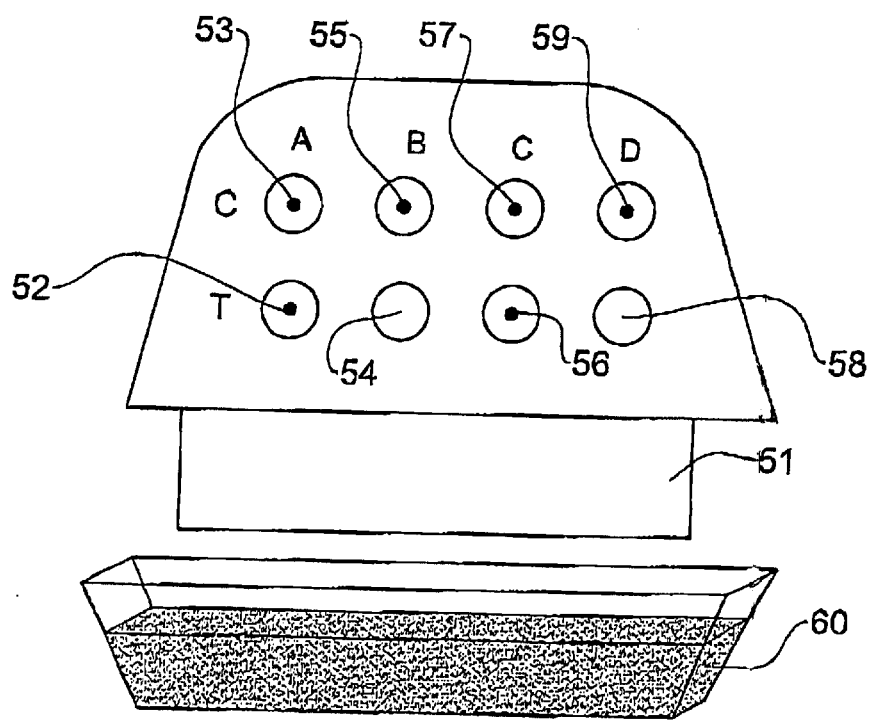
FIG. 3B shows a housing containing a substrate protruding out of the housing for detecting a plurality of parasites in the stool.

FIG. 3B shows a similar apparatus to that in 3A 50, having a protruding substrate therefrom as wick 51. However, in this case instead of having one indicator in the form of an opening test and one indicator for control, there are four indicators for the test (T) 52, 54, 56 and 58 and four indicators for the control (C) 53, 55, 57 and 59. After the sample has been diluted, it is poured to an elongated open vessel 60, and the protruding substrate 51 is dipped in this liquid containing vessel. Then, the liquid advances to the zones of the antibody of the test, or the zone containing, a priori, antigen-antibody aggregates of the control, and a color reaction may be determined. In the present case, as can be seen, the controls are appropriate, and the stool sample contains both parasites A and C indicated by the presence of colored dots.

What is claimed is:

1. A home and/or doctor's office test kit for detection of the presence of two or more fecal protozoan parasites in a stool sample, the kit comprising:
   (a) a vessel for mixing a stool specimen with a diluting liquid to produce a diluted stool specimen;
   (b) a housing holding within a substrate, the substrate comprising at least two separate zones containing antibodies against the parasites to be detected, the housing further comprising reagents for producing a visually detectable reaction when an antibody-parasite antigen complex is formed, the housing further comprising at least one conveying means for receiving diluted stool specimen and transferring it to the antibody containing zones of the substrate;
   (c) the housing further comprises at least one means for viewing the result of the antigen-antibody reaction;
   wherein the parasites are selected from the group consisting of *Amoeba histolytica, Amoeba hartmanni,*

*Amoeba coli, Amoeba nana, Giardia lamblia,* Cryptosporidium sp., *Blastocystis hominis, Chilomastix mesnili, Lodamoeba butschlii,* and *Dientamoeba fragillis.*

2. The kit according to claim 1, wherein the antibodies are immobilized on the substrate.

3. The kit according to claim 1, wherein the substrate has a capillary structure and the conveying means are the capillary forces of the substrate.

4. The kit according to claim 1, wherein the substrate has a porous structure and the conveying means are the absorbent forces of the substrate.

5. The kit according to claim 1, wherein the substrate is selected from the group consisting of nitrocellulose sheets, paper, gel-films, cellulose acetate, glass fibers, glass papers, and agarose gel.

6. The kit according to claim 1, wherein the at least one means for viewing is an opening in the housing above the antibodies-containing zones.

7. The kit according to claim 1, wherein the diluting liquid is selected from the group consisting of distilled water, formalin solution, sodium acetate solution, and sodium acetate solution with a detergent.

8. The kit according to claim 1, wherein the visually detectable reaction is obtained by binding of an antibody directed against the parasite to be detected, a component shed or secreted from the parasite reaction is obtained by binding of an antibody directed against the parasite to be detected, a component shed or secreted from the parasite, immunogenic epitopes of the parasites and combination thereof, the antibodies are conjugated to a detectable label to form an antibody-parasite antigen complex.

9. The kit according to claim 8, wherein detectable label is a gold particle.

10. The kit according to claim 8, wherein the detectable label is an enzyme capable in the presence of a suitable substrate, to produce a visually detected reaction.

11. The housing according to claim 1, comprising a plurality of means for viewing, each of said means is an opening in the housing above each of said separate zones.

12. The kit according to claim 1, wherein the antibodies are polyclonal antibodies.

13. The kit according to claim 1, further comprising a scooping device.

14. The kit according to claim 13, wherein the scooping device is an integral part of a cap for the vessel.

15. The kit according to claim 1, further comprising a disposable container for collecting a stool sample.

16. A method for detecting the presence of two ore more fecal protozoan parasites in a stool sample, the method comprising:
    (a) obtaining a stool specimen;
    (b) diluting the stool specimen with a diluting liquid to produce a diluted stool specimen;
    (c) introducing the stool specimen into a housing in the kit according to claim 1; and
    (d) detecting the presence or absence of the parasite in the stool specimen by observing the result of the antigen-antibody reaction.

17. The method according to claim 16, for detecting fetal parasites in an animal stool sample.

18. The method according to claim 17, wherein the animal is human.

19. The kit according to claim 1 wherein the substrate of the housing comprises a plurality of zones containing antibodies against all of the following parasites, each zone containing antibodies against one of the parasites: *Amoeba histolytica, Amoeba hartmanni, Amoeba coli, Amoeba nana, Giardia lamblia,* Cyptosporidium sp., *Blastocystis hominis, Chilomastix mesnili, lodamoeba butschlii,* and *Dientamoeba fragillis.*

20. The method according to claim 16 wherein the substrate of the housing of the kit in step (c) comprises a plurality of zones containing antibodies against all of the following parasites, each zone containing antibodies against one of the parasites: *Amoeba histolytica, Amoeba hartmanni, Amoeba coli, Amoeba nana, Giardia lamblia,* Cryptosporidium sp., *Blastocystis hominis, Chilomastix mesnili, lodamoeba butschlii,* and *Dientamoeba fragillis.*

\* \* \* \* \*